United States Patent [19]

Grötsch

[11] Patent Number: 5,298,620
[45] Date of Patent: Mar. 29, 1994

[54] PROCESS FOR THE DESTRUCTION OF CYANURIC FLUORIDE IN THE RESIDUES OBTAINED DURING ITS PREPARATION

[75] Inventor: Georg Grötsch, Bad Soden am Taunus, Fed. Rep. of Germany

[73] Assignee: Hoechst Aktiengesellschaft, Frankfurt, Fed. Rep. of Germany

[21] Appl. No.: 834,303

[22] PCT Filed: Aug. 18, 1990

[86] PCT No.: PCT/EP90/01363

§ 371 Date: Feb. 19, 1992

§ 102(e) Date: Feb. 19, 1992

[87] PCT Pub. No.: WO91/02727

PCT Pub. Date: Mar. 7, 1991

[30] Foreign Application Priority Data

Aug. 24, 1989 [DE] Fed. Rep. of Germany ....... 3927951

[51] Int. Cl.$^5$ ............................................. C07D 251/28
[52] U.S. Cl. ...................................... 544/217; 544/190
[58] Field of Search ................................. 544/190, 217

[56] References Cited

U.S. PATENT DOCUMENTS

| | | | |
|---|---|---|---|
| 2,937,171 | 5/1960 | Smith | 544/217 |
| 3,162,632 | 12/1964 | Olstowski | 544/217 |
| 4,329,458 | 5/1982 | Klauke et al. | 544/217 |
| 4,332,939 | 6/1982 | Seifert et al. | 544/217 |

FOREIGN PATENT DOCUMENTS 0035704 9/1981 European Pat. Off. .
2194238 3/1988 United Kingdom .

OTHER PUBLICATIONS

Seel et al. Chemische Berichte 92, 344, 1959.

*Primary Examiner*—Mukund J. Shah
*Assistant Examiner*—P. K. Sripada
*Attorney, Agent, or Firm*—Connolly & Hutz

[57] ABSTRACT

Process for the reliable and quantitative destruction of the residual cyanuric fluoride which still remains in residues from the cyanuric fluoride preparation by reaction of cyanuric chloride with alkali metal fluorides in dipolar aprotic solvents such as sulfolane, nitrobenzene, or benzonitrile after distillative removal of the majority of cyanuric fluoride; which comprises reacting the residue with an alkali metal hydroxide, bicarbonate or carbonate which is anhydrous apart from any water of crystallization present, or any desired mixture of these compounds, in an amount which is at least equivalent to the residual cyanuric fluoride at temperatures of about 20° to about 180° C.

20 Claims, No Drawings

PROCESS FOR THE DESTRUCTION OF CYANURIC FLUORIDE IN THE RESIDUES OBTAINED DURING ITS PREPARATION

The invention relates to a process for the reliable and quantitative destruction of cyanuric fluoride in the residues obtained during its preparation from cyanuric chloride and alkali metal fluorides in dipolar aprotic solvents.

It has been known for a long time that cyanuric fluoride can be prepared from cyanuric chloride using alkali metal fluorides, such as, for example, NaF (Tullock, Coffman, J. Org. Chem. 25, 2016 (1960) and European Patent 035,704) or KF or CsF (Japanese Patent 61,047,465) in dipolar aprotic solvents, such as, for example, sulfolane or benzonitrile, under anhydrous conditions. In this process, cyanuric fluoride is removed from the reaction mixture by distillation under normal pressure or in vacuo, if appropriate in the presence of an entraining agent. It serves as a useful precursor for agricultural chemicals, dyestuffs, optical brighteners, photochemicals and pharmaceuticals.

Industrial utilization of these processes has the great disadvantage that traces of cyanuric fluoride usually remain in the distillation residue, in addition to the alkali metal chloride formed, and that intermediate runnings containing cyanuric fluoride are obtained in the distillation of the cyanuric fluoride. Because of the high toxicity of cyanuric fluoride ($LC_{50}$ (inhalation-rats): 3.1 ppm; $LD_{50}$ (skin-rabbits): 160 ppm, J. Am. Ind. Hyg. Ass. 33, 382 (1972)), these residues therefore have to be detoxified before final disposal. Working up which may be carried out reusing the solvent, for example sulfolane, is likewise significantly easier and less expensive after destruction of the cyanuric fluoride, since the safety measures required for handling cyanuric fluoride can be dispensed with.

There was thus a need for a process in which not only the contents of HF which are present under certain circumstances, as in German Offenlegungsschrift 3,727,973 (=GB-A 2194238), are bonded, but in addition the residual cyanuric fluoride which still remains in the distillation residue or in distillation intermediate runnings can be reliably destroyed. Treatment of the distillation residues with milk of lime (Kühn-Birett, Merkblätter Gefährliche Arbeitsstoffe (leaflets on hazardous working materials), sheet no. C 73) is unsuitable for an industrial procedure, since after contamination with water the reaction vessels can be used again for the cyanuric fluoride preparation only after thorough cleaning—i.e. above all drying. The solvent must likewise be subjected to expensive drying before re-use.

It has now been found that the residual cyanuric fluoride which still remains in residues from the cyanuric fluoride preparation by reaction of cyanuric chloride with alkali metal fluorides in dipolar aprotic solvents after distillative removal of the majority of the cyanuric fluoride can be destroyed reliably and quantitatively by reacting the residue containing cyanuric fluoride with an alkali metal hydroxide, bicarbonate or carbonate which is anhydrous apart from any water of crystallization present, or any desired mixture of these compounds, in an amount which is at least equivalent to the residual cyanuric fluoride at temperatures of about 20° to about 180° C., preferably about 50° to about 140° C. and particularly preferably about 70° to about 130° C.

Possible alkali metal hydroxides, bicarbonates or carbonates are, for example, LiOH, NaOH, KOH, $NaHCO_3$, $KHCO_3$, $Na_2CO_3$ or $K_2CO_3$ or mixtures thereof.

If mixtures of alkali metal hydroxides, bicarbonates and carbonates are used, the components mentioned are used in the abovementioned amounts per mol of cyanuric fluoride in accordance with their proportion in the mixture.

The alkali metal compounds mentioned are added to the residues containing cyanuric fluoride either in bulk or in the form of a suspension of the alkali metal compound, preferably in the dipolar aprotic solvent used as the reaction medium, such as, for example, sulfolane, nitrobenzene or benzonitrile, or in another solvent which is inert under the reaction conditions and which can preferably be separated off by distillation from the dipolar aprotic solvent used as the reaction medium. Possible such inert solvents are aprotic solvents, such as, for example, toluene, chlorobenzene or dichlorobenzene.

The addition of the alkali metal compounds mentioned in bulk or in the form of a suspension in an aprotic solvent to the residue containing cyanuric fluoride is advantageously carried out continuously in portions, i.e. by metering.

As monitoring of the reaction by gas chromatography shows, cyanuric fluoride is no longer detectable after a short time, i.e. even traces of cyanuric fluoride are reliably destroyed.

Since no aqueous bases are used, contamination of the solvent and reaction apparatus with water is avoided.

The particular solvents used can be recovered by filtration or by distillation under normal pressure or in vacuo. The solvents recovered virtually quantitatively in this manner can be used again in the process or for the preparation of cyanuric fluoride. The residue of alkali metal chloride free from cyanuric fluoride, mixed with excess alkali metal fluoride, for example NaCl/NaF, KCl/KF, CsCl/CsF or any desired mixture of these alkali metal salts, obtained after removal of the solvent can then be stored or worked up without problems.

The compounds calcium hydroxide, calcium oxide, calcium carbonate, magnesium oxide or magnesium hydroxide which can often likewise be employed as bases are surprisingly far less suitable for degrading cyanuric fluoride rapidly and quantitatively (see Comparison Examples 7 to 11).

Moreover, it was not to be predicted that bases in the form of solids, such as alkali metal hydroxides, carbonates or bicarbonates, decompose cyanuric fluoride in a suitable manner without water being present, which is known to effect extremely rapid hydrolysis of cyanuric fluoride (Seel et al., Chem. Ber. 92, 344 (1959)).

The following examples serve to illustrate the invention, without limiting it thereto.

EXAMPLE 1

2.1 g of NaOH lozenges are added to a mixture of 21.0 g of sulfolane and 1.1 g of cyanuric fluoride at room temperature. After the mixture has been stirred for two hours, cyanuric fluoride is no longer detectable.

EXAMPLE 2

6.8 g of NaOH powder are added to a mixture of 68.9 g of sulfolane and 7.7 g of cyanuric fluoride at about 25° C. The cyanuric fluoride reacts quantitatively with the base (monitoring by gas chromatography) with a rapid rise in temperature to about 180° C.

EXAMPLE 3

19.8 g of $Na_2CO_3$ are added to a mixture of 68.9 g of sulfolane and 7.7 g of cyanuric fluoride at room temperature. The cyanuric fluoride reacts quantitatively with the base (monitoring by gas chromatography), $CO_2$ being evolved, in the course of 1.5 hours at about 25° to 40° C.

EXAMPLE 4

7.7 g of cyanuric fluoride are reacted with 28.6 g of $NaHCO_3$ as described in Example 3. After 1.5 hours, cyanuric fluoride is no longer detectable by gas chromatography.

EXAMPLE 5

A hot solution, at 100° C., of 369 g of cyanuric chloride in 500 g of sulfolane is added dropwise to a suspension of 384 g of potassium fluoride in 700 g of sulfolane, likewise at 100° C., in the course of 2 hours. The cyanuric fluoride is then distilled off under a pressure of 500 to 100 mbar. The yield is 257 g (95% of theory); content 99.4 area % (gas chromatography).

According to gas chromatography, the distillation residue still contains 1% by weight of cyanuric fluoride, based on the sulfolane. After addition of 40 g of sodium carbonate (calcined), the mixture is subsequently stirred at this temperature [sic] for a further 1 hour. Cyanuric fluoride is then no longer detectable by gas chromatography.

After the undissolved salts have been filtered off at 60° C., the sulfolane mother liquor is distilled under 27 bar/160° C. 1128 g of sulfolane are obtained. Together with the drying condensate of the potassium chloride/fluoride mixture, 98% of the sulfolane employed is recovered.

EXAMPLE 6

40 g of potassium carbonate are added at 100° C. to a distillation bottom product obtained as in Example 5 and the mixture is stirred at this temperature for 1 hour; cyanuric fluoride is then no longer detectable by gas chromatography.

EXAMPLE 7 (COMPARISON EXAMPLE)

2.0 g of calcium hydroxide are added to a mixture of 21.1 g of sulfolane and 1.0 g of cyanuric fluoride and the mixture is stirred at room temperature for 1 hour. According to gas chromatography, the cyanuric fluoride content has decreased from 4.5% by weight to 4.0% by weight, based on the liquid phase. Only after subsequent heating at 85° C. for 2 hours has the cyanuric fluoride content fallen to 1.9%, based on the sulfolane.

EXAMPLE 8 (COMPARISION EXAMPLE)

2.13 g of magnesium oxide are added to a mixture of 21.6 g of sulfolane and 1.1 g of cyanuric fluoride. The mixture is stirred at room temperature for 1 hour and then at 85° C. for 7.5 hours. After this time, the cyanuric fluoride content has fallen from originally 4.8% by weight to 1.2% by weight, based on the liquid phase.

EXAMPLE 9 (COMPARISON EXAMPLE)

10.8 g of magnesium hydroxide are added to a mixture of 68.9 g of sulfolane and 7.7 g of cyanuric fluoride and the mixture is stirred at room temperature for 3.5 hours and then at 100° C. for 2 hours. The cyanuric fluoride content has fallen from originally 10% by weight to 8% by weight, based on the liquid phase.

EXAMPLES 10 AND (COMPARISON EXAMPLES)

The base stated is added to a mixture of 68.9 g of sulfolane/7.7 g of cyanuric fluoride and the mixture is stirred first at room temperature and then at 100° C.

| Example | Base | Amount (g) | Reaction time at room temp. (h) | 100° C. (h) | Initial cyanuric fluoride, (% by weight) | Final concentration based on the liquid phase (% by weight) |
|---|---|---|---|---|---|---|
| 10 | CaO | 10.4 | 3.75 | 1.5 | 10 | 4.0 |
| 11 | $CaCO_3$ | 18.6 | 3.0 | 1.5 | 10 | 7.6 |

I claim:

1. A process for the reliable and quantitative destruction of the residual cyanuric fluoride which still remains in residues from the cyanuric fluoride preparation by reaction of cyanuric chloride with alkali metal fluorides in dipolar aprotic solvents after distillative removal of the majority of cyanuric fluoride, which comprises reacting the residue with an alkali metal hydroxide, bicarbonate or carbonate which is anhydrous apart from any water of crystallization present, or any desired mixture of these compounds, in an amount which is at least equivalent to the residual cyanuric fluoride at temperatures of 20° to 180° C.

2. The process as claimed in claim 1, wherein the reaction is carried out at temperatures of 50° to 140° C.

3. The process as claimed in claim 1, wherein the reaction is carried out at temperatures of 70° to 130° C.

4. The process as claimed in claim 1, wherein the residue is reacted with at least 3 mol of alkali metal hydroxide or bicarbonate per mol of cyanuric fluoride.

5. The process as claimed in claim 1, wherein the residue is reacted with at least 1.5 mol of alkali metal carbonate per mol of cyanuric fluoride.

6. The process as claimed in claim 4, wherein, in the reaction of the residue with a mixture of alkali metal hydroxide, bicarbonate and carbonate, these components are used in amounts as claimed in claim 4 per mol of cyanuric fluoride, according to their proportion in the mixture.

7. The process as claimed in claim 1, wherein the alkali metal hydroxide, bicarbonate or a carbonate or mixture thereof is added in bulk to the residue containing cyanuric fluoride.

8. The process as claimed in claim 1, wherein the alkali metal hydroxide, bicarbonate or carbonate or mixture thereof is added in the form of a suspension in an aprotic solvent, which can be separated off by distillation from the solvents used as the reaction medium, to the residue containing cyanuric fluoride.

9. The process as claimed in claim 1, wherein the alkali metal hydroxide, bicarbonate or carbonate or mixture thereof is added as a suspension in the dipolar aprotic solvent used as the reaction medium to the residue containing cyanuric fluoride.

10. The process as claimed in claim 1, wherein the residue containing cyanuric fluoride is added to the alkali metal hydroxide, bicarbonate or carbonate or mixture thereof.

11. The process as claimed in claim 5, wherein per mole of cyanuric fluoride in the residue, the residue is reacted with 1.5 mol of a mixture of alkali metal hydroxide, bicarbonate and carbonate components and the reaction between the cyanuric fluoride and each component in the mixture is proportional to the amount of alkali metal hydroxide, bicarbonate, and carbonate component in the mixture.

12. The process as claimed in claim 2, wherein:
the alkali metal hydroxide, bicarbonate, or a carbonate or mixture thereof is added to the residue containing cyanuric fluoride in bulk or in the form of a suspension in an aprotic solvent, said solvent being the same as, or capable of being separated off by distillation from, the solvent or solvents used as the reaction medium.

13. The process as claimed in claim 3, wherein:
the alkali metal hydroxide, bicarbonate, or a carbonate or mixture thereof is added to the residue containing cyanuric fluoride in bulk or in the form of a suspension in an aprotic solvent, said solvent being the same as, or being capable of being separated off by distillation from, the solvent or solvents used as the reaction medium.

14. The process as claimed in claim 4, wherein:
the alkali metal hydroxide, bicarbonate, or a carbonate or mixture thereof is added to the residue containing cyanuric fluoride in bulk or in the form of a suspension in an aprotic solvent, said solvent being the same as, or being capable of being separated off by distillation from, the solvent or solvents used as the reaction medium.

15. The process as claimed in claim 5, wherein:
the alkali metal hydroxide, bicarbonate, or a carbonate or mixture thereof is added to the residue containing cyanuric fluoride in bulk or in the form of a suspension in an aprotic solvent, said solvent being the same as, or being capable of being separated off by distillation from, the solvent or solvents used as the reaction medium.

16. The process as claimed in claim 2, wherein:
the residue containing cyanuric fluoride is added to the alkali metal hydroxide, bicarbonate or carbonate or mixture thereof.

17. The process as claimed in claim 3, wherein:
the residue containing cyanuric fluoride is added to the alkali metal hydroxide, bicarbonate or carbonate or mixture thereof.

18. The process as claimed in claim 4, wherein:
the residue containing cyanuric fluoride is added to the alkali metal hydroxide, bicarbonate or carbonate or mixture thereof.

19. The process as claimed in claim 5, wherein:
the residue containing cyanuric fluoride is added to the alkali metal hydroxide, bicarbonate or carbonate or mixture thereof.

20. The process as claimed in claim 1, wherein the polar aprotic solvent is selected from the group consisting of sulfolane, benzonitrile, and nitrobenzene.

* * * * *